(12) United States Patent
Sarkar et al.

(10) Patent No.: US 6,920,412 B1
(45) Date of Patent: Jul. 19, 2005

(54) REAL TIME LIFE MODELS FOR AUTOMATIC TRANSMISSION FLUIDS

(75) Inventors: Reuben Sarkar, Graz (AT); Brent D. Calcut, Allen Park, MI (US); James L. Linden, Rochester Hills, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/765,239

(22) Filed: Jan. 26, 2004

(51) Int. Cl.$^7$ .............................................. G06F 15/00
(52) U.S. Cl. ...................... 702/181; 702/156; 73/53.05
(58) Field of Search ................................ 123/676, 484, 123/568.19, 454, 494; 73/53.05; 702/156, 181

(56) References Cited

U.S. PATENT DOCUMENTS

| | | | |
|---|---|---|---|
| 4,742,476 A | 5/1988 | Schwartz et al. | |
| 4,847,768 A | 7/1989 | Schwartz et al. | |
| 5,777,211 A | 7/1998 | Binienda et al. | |
| 6,327,900 B1 | 12/2001 | McDonald et al. | |
| 2004/0117147 A1 | * 6/2004 | Hirthe et al. | ................ 702/181 |

* cited by examiner

*Primary Examiner*—John Barlow
*Assistant Examiner*—Stephen J. Cherry
(74) *Attorney, Agent, or Firm*—Leslie C. Hodges

(57) ABSTRACT

The remaining useful life of a transmission fluid in a vehicle is continually estimated by a transmission control computer module during vehicle operation using both an oxidation model and a shift energy model. The oxidation model uses experimentally determined remaining useful fluid life values obtained at temperatures experienced by the fluid in transmission usage and subtracts incremental values from said life based on the temperature-time experience of volume fractions of the fluid in the sump and torque converter. The shift energy model starts with an estimated maximum number of shifts and continually obtains a current remaining useful life by deducting for actual shifts and estimated shift energy inputs based on fluid temperature. Notice of end of fluid useful life is given when one of the models first determines no remaining useful fluid life.

8 Claims, 2 Drawing Sheets

REAL TIME LIFE MODELS FOR AUTOMATIC TRANSMISSION FLUIDS

TECHNICAL FIELD

This invention pertains to mathematical models for on-vehicle determination of the remaining useful life of its automatic transmission fluid. More specifically, this invention pertains to the development and use of a combination of a temperature-based oxidation model and a friction model based on transmission gear shifts for determining remaining useful life of the fluid.

BACKGROUND OF THE INVENTION

Automatic transmissions have long been employed in automotive vehicles for transmission of engine torque to the drive wheels of the vehicle. These transmissions are controlled to execute shifting between several gear ratios depending on engine speed and operator commanded vehicle speed. Automatic transmissions have used a hydraulic fluid for transmission of torque between rotating driving and driven members of the device. This automatic transmission fluid (ATF) is subjected to considerable shear forces in the operation of the torque converter and transmission.

Automatic transmission fluids typically comprise a base oil with additives to slow thermal degradation of the oil. An ATF is heated due to the energy that is put into it during operation of the torque converter and transmission as well as heat from the engine compartment environment. The fluid may experience temperatures of 160° C. or higher. Over the past decades, vehicle manufacturers have recommended ATF change intervals of 50,000 miles, 100,000 miles, or fill for life depending on severe, normal or mild operating conditions, respectively.

Now the trend in vehicle requirements is for smaller sump transmissions, more aggressive shift calibrations and lower cooling capacity. These requirements mean that an ATF may experience a more severe operating environment, resulting in faster degradation due to oxidation and high shift energy input. These more severe demands on the fluid may require shorter, less predictable change periods. Accordingly, it is an object of this invention to provide a method for on-vehicle computer execution for predicting the end of the useful life of a vehicle's ATF and for advising the vehicle operator to change the fluid.

SUMMARY OF THE INVENTION

This invention provides two mathematical models that are conducted in parallel on an electronic transmission control microprocessor to determine the remaining useful life of a vehicle's transmission fluid. The models are suitably incorporated into the transmission computer controller, which is already programmed to control the operation of the transmission in response to driver commands. Such a transmission controller may be part of an engine/transmission powertrain control module (PCM). In accordance with the invention, two ATF models are used in parallel to better assess the state of the ATF without impairing the efficiency and responsiveness of the microprocessor.

One of the models is an oxidation model starting with an experimentally-determined life of the specific ATF composition. The oxidation model tracks the temperature experiences of portions of the ATF in different parts of the transmission to project (i.e., calculate) the remaining useful life of the bulk fluid. The other model is a friction degradation model that continually tracks current transmission shift energy, at the current bulk fluid temperature, imparted to the fluid for each upshift/downshift of the transmission. For many fluids it is necessary or desirable to consider both the oxidation of the bulk oil and its friction properties to reliably determine its remaining useful life. When one of the two models first determines that useful fluid life has been depleted, the vehicle operator is advised to change the ATF. These two models complement each other both in reliably estimating the remaining useful life of the fluid and in efficient use of the PCM.

The bulk oxidation model is preferably developed for each specific ATF composition. Samples of the fluid are subjected to oxidation in heated open aluminum beakers at temperatures spanning the temperature range that the fluid will experience in operation of the automatic transmission in which the fluid is to be used. The extent of fluid oxidation is measured in the content of each beaker preferably using the change in total acid number, delta TAN, via ASTM D664, initially and at suitable time intervals of the test. An increase in total acid number of, for example, 2.5 mg potassium hydroxide per gram of fluid (mg KOH/g) may be taken as indicating the end of the useful life of the fluid sample. The useful life of the ATF composition at each temperature is thus determined. Such data is plotted in linear form as a graph of the natural logarithm of the time (t) to end of useful fluid life (when ΔTAN=2.5 mg KOH/g) against the reciprocal of the beaker test temperature (T) in degrees Kelvin. The linear plot of Equation (1):

$$Ln(t) = A + \frac{B}{kT}$$

yields intercept, A, and slope, B, as oxidation parameters of the specific fluid that are used in the thermal oxidation model. The constant, k, is a proprietary parameter incorporated to account for increase transmission severity over the beaker test method.

In an operating transmission, portions of the total fluid volume are circulated from the sump into the torque converter and into the torque converter clutch interface. At any moment of transmission operation, the fluid volume fraction at the clutch interface is often experiencing the highest level of current energy input while the balance of the fluid in the converter is also experiencing shear and is being heated. More of the fluid is in the transmission sump and the temperature in the sump fluid represents the recent energy input history of the transmission and the working ATF. When the vehicle is being driven, the fluid volumes circulating through the torque converter and torque converter clutch are heated and carry that heat into the contents of the sump. In a preferred embodiment of the invention, the oxidation model recognizes the different, usually higher, temperatures of the volume fractions of the fluid in the torque converter and the clutch for their deleterious effect on the remaining life of the ATF. Equation 1 is used in an expanded form to account for the different temperatures in the sump, torque converter and torque converter clutch.

In a preferred embodiment of the invention, and for microprocessor efficiency, Equation 1 is used to calculate a remaining useful life (RUL) for the ATF in this oxidation model at a reference temperature such as 80° C. The equation is then used to calculate penalty factors (PF) for fluid temperatures different from the reference temperature. During transmission operation, the microprocessor continually reads transmission sump temperatures, over successive processor sequences, and applies the penalty factor for the fraction of the fluid in the sump. Successively higher temperatures and penalty factors are used for the volume fractions of the fluid in the torque converter (TC) portion of the transmission and in the torque converter clutch (TCC) portion, respectively. The three reduction values (sump+ TC+TCC) in fluid life are subtracted from initial value of fluid life and the sequence is repeated for the oxidation model during transmission operation events until there is no remaining useful ATF life.

In parallel with the ATF oxidation model, the PCM also executes a shift event friction model. An initial determination of lifetime shifts for the ATF at a reference temperature is made. The reference temperature may, for example, be a transmission sump temperature of 80° C. During PCM processing cycles for this model, a record of all shift events is made together with average sump temperature over the time interval of the cycle. Shift events include $1^{st}$ gear to $2^{nd}$ gear upshift/downshift, $2^{nd}$ gear to $3^{rd}$ gear upshift/downshift, etc., over the whole range of forward speed gears of the transmission. A shift energy input to the ATF is determined and associated with each shift correlated to the sump temperature. The microprocessor correlates stored shift energy values with each shift and reduces the value of the remaining number of shifts by the appropriate amount based on shift energy input to the ATF. This microprocessor executed process, like the oxidation model, is continued until one model yields no useful remaining ATF life.

It has been found that the combination of the above-described oxidation model and shift energy models provide a reliable, useful and microprocessor efficient method for determining the remaining useful life of an automatic transmission fluid. This parallel model approach does not understate the remaining life so that unnecessary ATF changes are made. And the model protects the transmission itself.

Other objects and advantages of the invention will be understood from a description of a preferred embodiment of the invention which follows.

DESCRIPTION OF PREFERRED EMBODIMENTS

Figure 1:
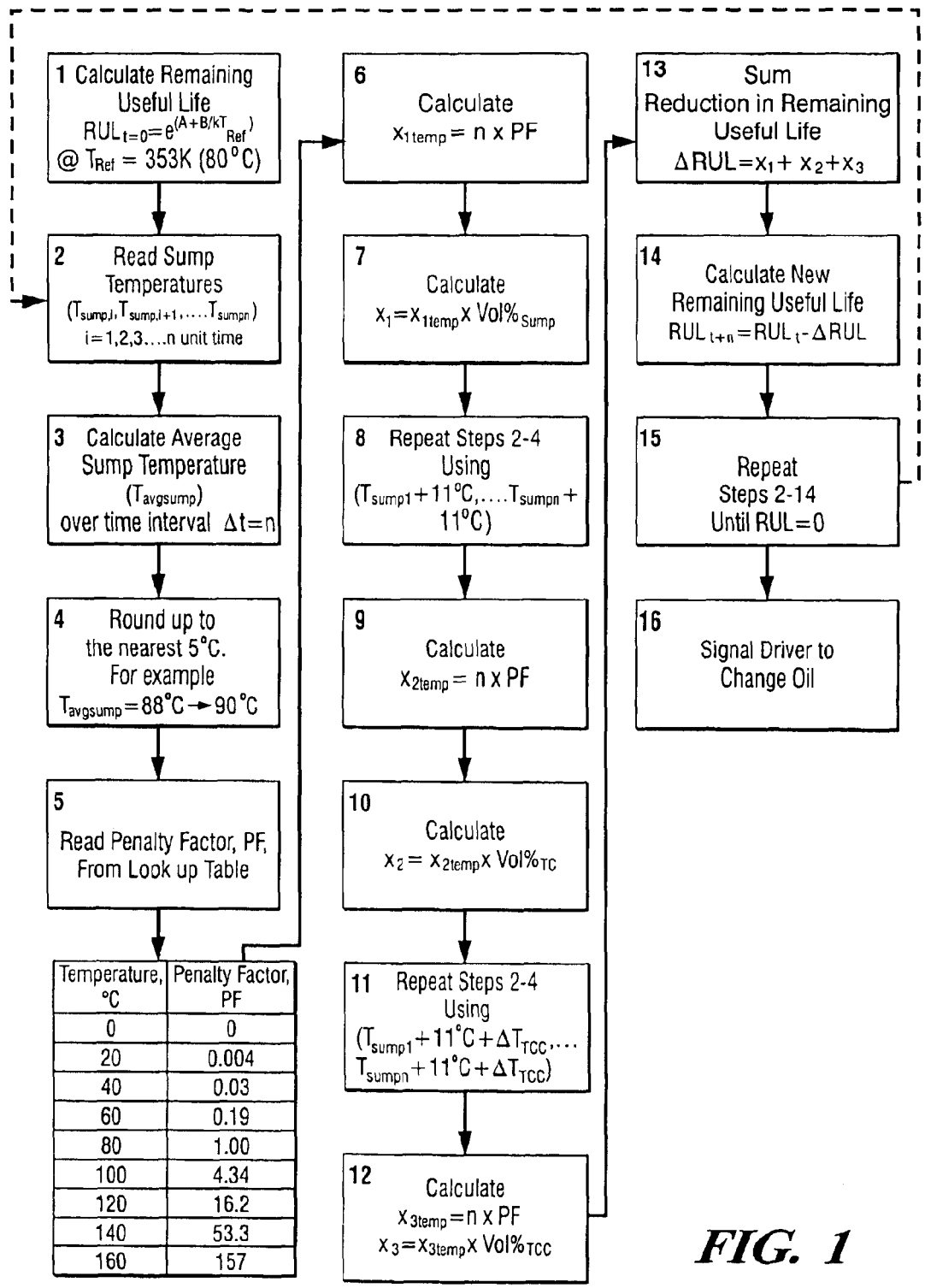
FIG. 1 is a process flow diagram of a preferred method for calculating remaining useful life of a transmission fluid by a fluid oxidation model.

Automatic transmission fluids exhibit a finite useful life due to oxidative degradation of the base oil and additive package. One common metric for assessing the general quality of current formulation type transmission oil is to measure the extent of bulk fluid oxidation as reflected in an increase in the total acid number (delta TAN) of the fluid via ASTM D664. Based upon historical data correlating to increased shudder tendency and loss of frictional performance, ATFs exhibiting an increase in TAN of 2.5 mg KOH/g are considered to be at the end of their useful life. The rate of bulk oxidation differs between oils and is a function of time at temperature in the presence of an oxidizing environment, the base oil chemistry, and the additive package formulation. In addition to loss of performance through bulk oxidation of the base oil, friction modifiers, present in minute concentrations, can also oxidize in the bulk fluid or locally at clutch interfaces without contributing appreciably to an increase in delta TAN.

Currently vehicle owner's manuals often specify three recommendations for transmission oil change intervals depending upon driver behavior, namely 50,000 miles, 100,000 miles, and fill for life (no change). However, oils can reach their end of useful life at different mileages. In addition, more aggressive usage of transmission systems in some applications has led to increased operating temperatures, which could reduce useful fluid life to mileages below the severe service recommendation of 50,000 miles. To account for this, transmission oil life algorithms, based upon bulk oxidation, have been implemented in vehicle transmission applications but they have not accurately tracked the condition of the ATF.

A new enhanced oil life algorithm has been developed to provide accurate feedback to vehicle operators of the oil change interval recommended for their driving behavior and transmission application. The model integrates two parallel approaches to determining end of useful fluid life, namely bulk oxidation due to time at temperature and specific degradation of frictional performance due to transmission shift events. Preferably, the oxidation model uses temperature information from more than one region of the operating transmission.

Oxidation Model

The bulk oxidation model was developed by subjecting ATFs to an Aluminum Beaker Oxidation test (ABOT) at 140° C., 150° C., 155° C., and 160° C. The extent of fluid oxidation was measured as the change in total acid number, delta TAN, via ASTM D664 at time intervals of 0, 150, 200, 250, and 300 hours. The average delta TAN of three repeat runs was plotted versus time for each fluid at each temperature. Linear functions were fit to the resulting plots. The slope of the fit lines were taken as the oxidation rate, delta TAN/hour, of the fluid. The time to the end of useful fluid life in hours at a given temperature was determined by dividing an end of useful fluid life, delta TAN of 2.5 mg KOH/g fluid, by the oxidation rate. The data was then linearized by plotting the natural log of the time to end of useful fluid life against the reciprocal of the ABOT test temperature in degrees Kelvin.

The slope and intercept of this line were the set as the fluids characteristic A and B oxidation parameters that subsequently were used in the thermal model as described in the following Equation 1:

$$Ln(t) = A + \frac{B}{kT},$$

where t is the time to fluid failure in hours, T is the fluid temperature in degrees Kelvin, A and B are parameters that describe the oxidation behavior of a particular ATF and k is a proprietary parameter incorporated to account for increased transmission severity over the bench test environment.

This base equation could be written as follows for the temperatures that would be seen in the transmission sump, torque converter and torque converter clutch interface as shown in the following Equation 2:

$$\ln(t)_{SUMP} = A + \left(\frac{B}{k * T_{sump}}\right)$$

$$\ln(t)_{CONVERTER} = A + \left(\frac{B}{k * T_{converter}}\right)$$

-continued $$\ln(t)_{TCC\ INTERFACE} = A + \left(\frac{B}{k * T_{TCC}}\right)$$

The exponential of the natural log of time to fluid failure for each regime was then calculated resulting in a time to fluid failure in hours for each transmission subsystem as shown in Equation 3:

$$t_{failure,\ i} = e^{ln(t)}$$

where i is determined for sump, torque converter and TCC interface.

The time to fluid failure for the three subsystems was then summed by weight averaging each subsystem on a percent volume basis as shown in Equation 4:

$$t_{Total} = \left(\frac{SumpVol.}{TransTotalVol}\right) * t_{Sump} + \left(\frac{ConverterVol.}{TransTotalVol}\right) * t_{TC} + \left(\frac{TCCVol.}{TransTotalVol}\right) * t_{TCC}$$

A particular transmission may, for example have an ATF capacity of eight liters. At a given moment in the operation of the transmission, approximately 1.5L of fluid may be in the torque converter with an additional 0.5 liter in the torque converter clutch. The balance is presumed to be in the sump for purposes of these models. The volume percentages of fluid in the respective portions of the transmission are, of course, based on the total volume of eight liters.

The value of the parameter k was determined by correlating temperature histograms and fluid oxidation levels from a commercial transmission vehicle test. The value of k was varied until the calculated time to end of useful fluid life was equal to the actual time to end of useful fluid life.

The values for characteristic oxidation parameters A and B for three different commercial automatic transmission fluids and the severity factor, k, for a production transmission are listed in the following Tables 1 and 2. Fluid 1 uses an API Group II base oil and Fluid 2 uses an API Group I base oil.

TABLE 1

| Characteristic Fluid | Oxidation Parameters A | B | Severity Factor k |
|---|---|---|---|
| 1 | −18.643 | 10787 | 1.116 |
| 2 | −32.099 | 16009 | 1.116 |

TABLE 2

| Fluid | Reference Temperature | Reference Remaining Useful Life Hours | Seconds |
|---|---|---|---|
| 1 | 80° C./353K | 6191.3 | 22,288,680 |
| 2 | 80° C./353K | 5047.5 | 18,171,000 |

Using these values, the remaining useful fluid life was calculated across the range of expected transmission operating temperatures. From these values a reference temperature of 353K (80° C.) was arbitrarily assigned. Look-up tables displaying penalty factors were generated by normalizing remaining useful fluid life against the reference remaining useful fluid life. Examples of these tables can be seen in the following table.

TABLE 3

| Temperature | | Penalty Factors | |
|---|---|---|---|
| Celsius | Kelvin | Fluid 1 | Fluid 2 |
| −40 | 233 | 0 | 0 |
| −20 | 253 | 0 | 0 |
| 0 | 273 | 0 | 0 |
| 20 | 293 | 0.004 | 0 |
| 40 | 313 | 0.03 | 0.006 |
| 60 | 333 | 0.19 | 0.09 |
| 80 | 353 | 1.00 | 1.00 |
| 100 | 373 | 4.34 | 8.83 |
| 120 | 393 | 16.2 | 62.5 |
| 140 | 413 | 53.3 | 366 |
| 160 | 433 | 157 | 1820 |
| 180 | 453 | 421 | 7850 |

The model works by subtracting units of time multiplied by the penalty factor from the reference remaining useful life for the applicable fluid. For example, for fluid 1, every second spent at the reference temperature of 353K (80° C.), one second is subtracted from the remaining useful fluid life. However, for every second spent at 373K (100° C.), 4.34 seconds is subtracted from the reference remaining useful fluid life. When the reference remaining useful fluid life reaches a value of zero, the algorithm signals the driver that it is time to change the oil. A detailed process flow diagram of a preferred on-vehicle computer executable process for using the oxidation model to estimate the remaining useful life of an ATF is shown in FIG. 1. Definitions of the variables used in the FIG. 1 flow diagram follow:

Definition of Variables—FIG. 1

$RUL_{t=0}$=The remaining useful fluid life for unused ATF at the reference temperature.

$\Delta RUL$=The total reduction in remaining useful life over time interval n.

$RUL_{t+n}$=The calculated remaining useful life after a time interval n.

$T_{sump,i}$=The sump temperature at time i, where i could be in seconds or hours, falls within the interval i=1 to n.

$T_{avgsump}$=The average sump temperature over time interval, n.

$\Delta T_{TCC}$=The estimated temperature difference between the fluid in the torque converter and the fluid at the torque converter clutch interface.

PF=Penalty factor for a given fluid found in look-up table.

$x_{1temp}$=Dummy (i.e., temporary) variable assigned to hold the pre-weight averaged reduction in the remaining useful fluid life in the sump at the average temperature over time interval n.

$x_{2temp}$=Dummy (i.e., temporary) variable assigned to hold the pre-weight averaged reduction in the remaining useful fluid life in the torque converter at the average temperature over time interval n.

$x_{3temp}$=Dummy (i.e., temporary) variable assigned to hold the pre-weight averaged reduction in the remaining useful fluid life at the TCC interface at the average temperature over time interval n.

$x_1$=Volumetrically weight averaged contribution of reduction in remaining useful life due to the sump.

$x_2$=Volumetrically weight averaged contribution of reduction in remaining useful life due to the torque converter.

$x_3$=Volumetrically weight averaged contribution of reduction in remaining useful life due to the TCC interface.

FIG. 1, Block 1 indicates the calculation of the useful life of a specific unused ATF material at a reference temperature, $T_{ref}$, in this example, 353K (80° C.). The calculation is based on beaker oxidation data as described above and using Equations 1–4. Usage of the fluid results in reductions from its original or initial useful life. This determination of fluid life is stored in the memory of the PCM or like on-vehicle computer.

During operation of the vehicle, the PCM performs its processing cycles, each second or so, and receives a temperature input from a suitable sensor in the fluid sump of the transmission. Block 2 indicates the reading of the temperatures of the fluid in the sump, $T_{sump,i}$ over a brief suitable time period. In Block 3 the average temperature, $T_{avgsump}$, of the fluid in the sump is calculated. In this example, the average sump temperature, $T_{avgsump}$, is also used in the parallel friction model as described with respect to step 2 of FIG. 2.

In Block 4, the average sump temperature value, $T_{avgsump}$, is rounded up to the nearest 5° C. for reading the predetermined penalty factor, PF, in a prepared look-up table as indicated in Block 5. An excerpt of a look-up table, prepared as described above, is shown between Blocks 5 and 6 in FIG. 1.

The computer then calculates a reduction in the useful life of the fluid due to its temperature experience over time interval, n, by multiplying n by the PF for the $T_{avgsump}$ for the interval (Block 6). The product of this calculation, $x_{1temp}$, represents an estimated reduction in remaining life of the ATF if the total volume of the fluid was at the temperature of the sump. The variable, $x_{1temp}$, is temporarily held as a dummy variable for correction in accordance with the volume percent of the fluid in the sump. This calculation is made in Block 7 of FIG. 1. The volume percentage of the fluid in the sump is known for a particular transmission and may be considered a constant throughout transmission operation or corrected for different operation conditions and temperatures. The value obtained in Block 7 is temporarily stored in computer memory pending similar fluid life reduction calculations for the volume fractions of the fluid in the torque converter (TC) and the torque converter clutch (TCC) interface.

Commencing with Block 8 the transmission controller determines the reduction in useful fluid life attributable to the temperature experience of the volume fraction of ATF in the torque converter. If continuous temperature measurements of the fluid in the TC are available, these values can be used in the process. However, temperature sensors may not have been incorporated in the TC or the TCC, and it is desirable that temperature estimates be made for these portions of the ATF because they experience high temperatures that contribute significantly to the reduction of useful fluid life by oxidation.

In this example, the temperature of the fluid volume in the TC was estimated to average about 11° C. above the sump volume temperature. Thus, Block 8 repeats the steps of Blocks 2–4 except that 11 degrees Celsius are added to the measured sump volume temperature. An average TC temperature over the time interval is determined and rounded to obtain a penalty factor PF for the TC volume. Block 9 applies the PF to obtain a dummy value, as in Block 6, value $x_{2temp}$ for correction by the volume percentage of fluid in the TC. This is performed in Block 10.

The steps performed in Blocks 11 and 12 estimate a reduction in fluid life for the volume fraction at the TCC interface using an estimated average temperature at the TCC interface relative to the TC temperature. In Block 11, $\Delta T_{TCC}$ is added to the estimated TC temperature, $T_{sump}+11°$ C., where $\Delta T_{TCC}$ is typically a function of the power, in kW, transferred through the TCC. For example, in a 6.0L engine/300 mm converter application, $\Delta T_{TCC}=57.6*P_{TCC}-15.6$ for $\Delta T_{TCC}>0$. Often the temperature of the fluid at the TCC interface is slightly higher than the fluid volume in the TC.

In Block 13 the total reduction in remaining useful fluid life over the time interval $\Delta t$ is obtained by adding the reductions for the fluid volume percentages in the sump, TC and TCC interface. Thus, $\Delta RUL=x_1+x_2+x_3$. In Block 14 the computer calculates the new remaining useful life of the fluid by subtracting the currently determined reduction in fluid life due to oxidation from the previous cycle useful life value, indicated by the equation $RUL_{t+n}=RUL_t-\Delta RUL$. The value for $RUL_{t+n}$ becomes $RUL_t$ in the next iteration from which a new $\Delta RUL$ will be subtracted. Thus, RUL continually decreases as the algorithm runs.

As indicated in oxidative model process Block 15, the computer cycling continues during transmission use and the steps of Blocks 2–14 are repeated until RUL=0. When RUL=0, a signal is commanded to notify the vehicle operator to change the ATF. However, in accordance with this invention, a parallel computer process is being executed with a friction model accounting for shift energy input and the "change ATF" signal is given when one of these parallel processes first determines that RUL=0.

Friction Degradation Model

A friction degradation model is developed by subjecting an ATF to an SAE #2 Test Apparatus plate friction test using a modified DEXRON®-III test procedure. A $3^2$ design of experiment, shown in the following table, was set up with shift energy and bulk fluid temperature as the two variables.

| Design of Experiment for Friction Degradation Model | | |
| --- | --- | --- |
| Experiment | Shift Energy | Temperature |
| 1 | − | − |
| 2 | − | 0 |
| 3 | − | + |
| 4 | 0 | − |
| 5 | 0 | 0 |
| 6 | 0 | + |
| 7 | + | − |
| 8 | + | 0 |
| 9 | + | + |

The fluid is run until frictional performance degrades to unacceptable levels as determined by a rapid decrease in midpoint torque below the DEXRON®-III specification limit and/or a slow decrease in midpoint torque to levels below a critical lower limit. The number of shift events which occurred prior to end of useful fluid life are calculated based upon the number of test cycles completed and the data will be fit using statistical analysis software to a general equation of the form shown below as Equation 5:

$$y=a_o+a_1x_1+a_2x_2+a_3x_1x_2+a_4x_1^2+a_5x_2^2+a_6x_1^2x_2+a_7x_1x_2^2+a_8x_1^3+\ldots$$

The specific equation for a specific fluid follows as Equation 6:

$$TNS=878000-2455*T-66330*E+1410*E^2+82*T*E$$

where

TNS=Total number of shifts until end of useful remaining fluid life,

T=The temperature of fluid in the sump, and

E=Estimated shift energy from a look-up table.

The model is equated to actual transmission performance by correlating to data gathered on a DEXRON®-III commercial transmission cycling test. If necessary, parameters are added to adjust to severity of the model to agree with the cycling test data. The model is then implemented into an algorithm similar to the bulk oxidation model to calculate remaining fluid life through a parallel path. The model works by counting the number and type of shift events occurring over a given time interval. Using the preset shift energies for each type of shift event and the average sump temperature over that interval (already calculated by the bulk oxidation model), the remaining number of shifts a fluid can experience before end of useful life at those conditions is determined.

Shift energy is generated when a transmission is shifted between gears. At the start of a shift, the clutch or band being applied is slipping at a known speed. At the end of a shift this slip speed is reduced to zero. Shift energy is the amount of energy generated in the process of eliminating this slip. To calculate the shift energy, a vehicle is instrumented and the following parameters are recorded: transmission sump temperature, transmission input and output speed, commanded gear, clutch pressure for the oncoming clutch for the shift, and vehicle acceleration. This data is then used with transmission hardware constants to calculate the clutch slip versus time and clutch-apply force versus time for the shift. Knowing the clutch-slip and clutch-apply force, the power generated in the clutch is calculated. This power is the shift energy used in the FIG. 2 friction process.

The preset shift energy data for each type of shift is normalized against the remaining number of shifts at a reference temperature and multiplied by the number of specific shift events (i.e, number of 1–2 up shifts), which have occurred over that time interval. This is done for all types of shift events, such as 1–2, 2–3, and 3–4 up shifts, and the reduction in the remaining number of shifts over that time interval due to all shift events is summed and subtracted from the remaining number of shifts to end of useful life. When the counter equals zero, the driver is notified to change the oil. In this algorithm, more than one look-up table would be required. In order to save PCM space, calculations were done as needed. Also, although the bulk oxidation model runs in parallel with the friction degradation model, the average sump temperature calculated over a given time interval in the bulk oxidation model are shared with the friction degradation model.

Figure 2:
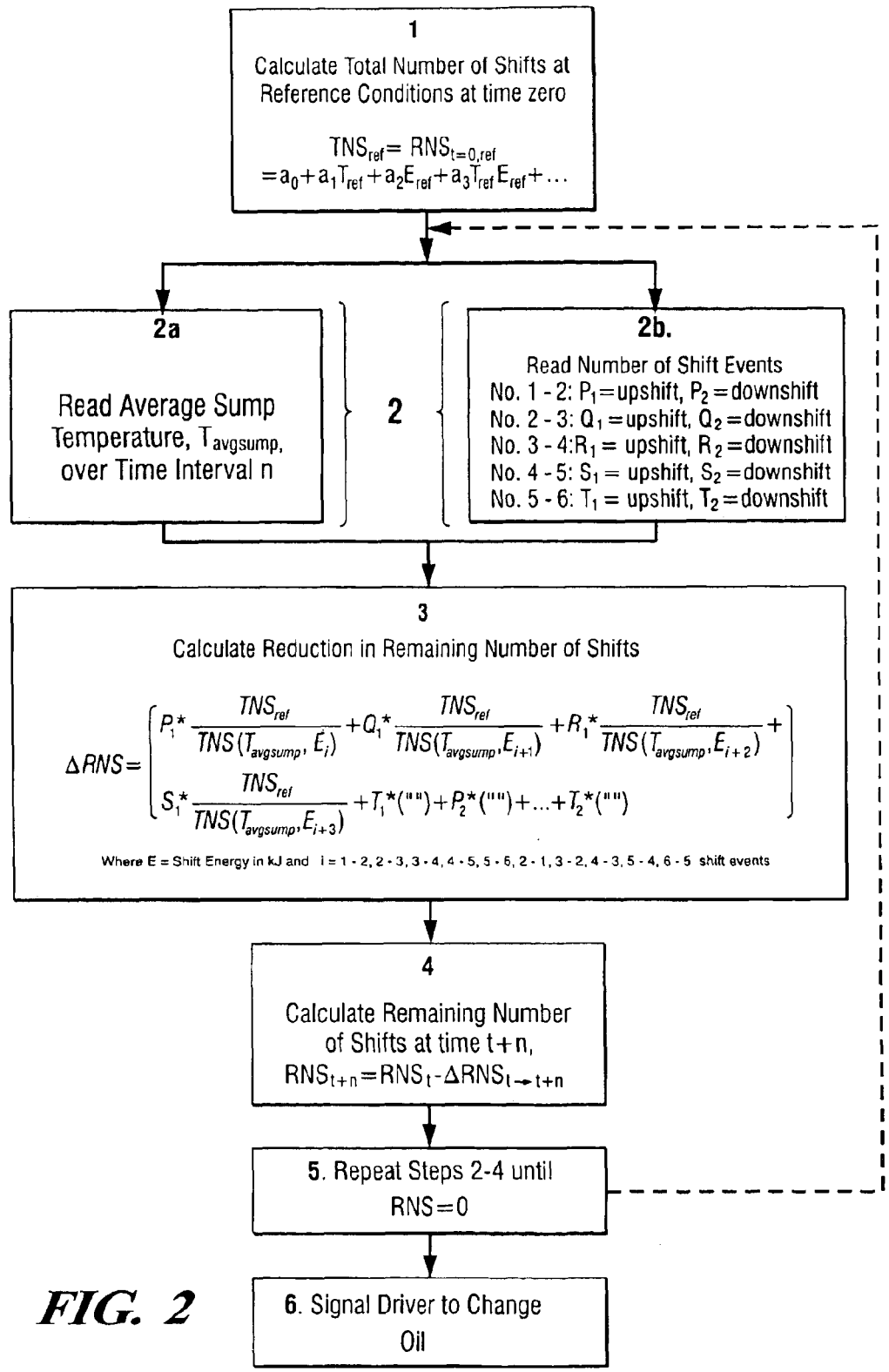
FIG. 2 is a process flow diagram of a preferred method for calculating remaining useful life of a transmission fluid using a shift energy input model.

A process flow diagram of a preferred method of computer execution of determining remaining shift life is presented in FIG. 2. In this example, an automatic transmission with six forward speeds is modeled. Such a transmission normally experiences more frequent gear shifts than transmissions with fewer forward gears. The definition of variables referred to in FIG. 2 follow in the next paragraphs.
Definition of Variables—FIG. 2.

$TNS_{ref}$=Total number of shifts for an unused ATF at the reference temperature and shift energy.

$T_{ref}$=Predetermined reference temperature in Kelvin.

$E_{ref}$=Predetermined reference shift energy in kJ.

RNS=Remaining number of shifts before end of useful fluid life.

$\Delta RNS_{t \rightarrow t+n}$=Reduction in the remaining number of shifts over time interval n.

$TNS(T_{avgsum}, E_i)$=Abbreviation for total number of shifts as a function of average sump temperature and shift energy.

$T_{avgsump}$=Average sump temperature in Kelvin over time interval, n.

$E_i$=Shift energy for a given shift i, kJ.

P, Q, R, S, T=The number of 1–2, 2–3, 3–4, 4–5, and 5–6 shifts respectively, including corresponding downshifts, over time interval n.

An initial number of gear shifts for an unused fluid is estimated or determined at a reference temperature, for example, 353K (80° C.). This may be done using a process like that summarized above resulting in Equation 5. Equation 6 is a specific example of an equation that may be used for this purpose. In FIG. 2, this step is indicated in Block 1 and the resulting value of $TNS_{ref}$ is stored in the database of the computer.

In the step 2 of the FIG. 2 friction model process, Blocks 2a and 2b, the current average sump fluid temperature over a selected time interval, n, is noted (Block 2a) from FIG. 1 (Block 3). Concurrently, all forward shift events, upshift or downshift, during the same time interval, n, are read, Block 2b. Shifts in and out of neutral are found to have negligible effect on the useful life of the ATF and are not recorded in this friction model. Downshifts are considered as imparting less shift energy into the transmission converter clutch than upshifts. Downshifts may be considered to impart half the energy input of a corresponding upshift. Accordingly, in Block 2b, shift events during a time interval are recorded respectively as $P_1$, upshift first to second gear; $P_2$, downshift second to first gear; $Q_1$, upshift second to third gear; $Q_2$, downshift third to second gear; $R_1$, upshift third to fourth gear; $R_2$, downshift fourth to third gear; $S_1$, upshift fourth to fifth gear; $S_2$ downshift fifth to fourth gear; $T_1$, upshift fifth to sixth gear; and $T_2$, downshift sixth to fifth gear.

Knowing the current average sump temperature and the respective shifts, a calculation of the reduction in remaining number of shifts ($\Delta RNS$) is made to account for the reduction in fluid life due to shift energy input, i.e., friction degradation. This calculation is suitably made using a model as indicated in Block 3 of FIG. 2. The model uses a predetermined shift energy, E, in kJ at an average sump temperature, $T_{avgsump}$. The shift energies for the respective upshifts vary by vehicle application, are dependent on throttle position at the moment of the upshift and can be stored as a look-up table. As stated, the shift energies for the respective downshifts are half the values of the corresponding upshifts at the throttle position.

The determination of friction degradation is based on the shift energy and temperature of the fluid in the sump as described above. Thus, a value of the current $\Delta RNS$ over current time interval n is calculated. The process moves to Block 4 of FIG. 2, which illustrates the calculation of the remaining number of shifts that the ATF can tolerate at time t+n. As shown in Block 4, the calculation is $RNS_{t+n}=RNS_t-\Delta RNS_{t \rightarrow t+n}$.

The steps of Blocks 24 are repeated as indicated in Block 5 until RNS=0, provided that the parallel oxidation process does not produce RUL=0 first. If the calculation of Block 5 reaches zero, notice is given to the vehicle operator (Block 6) to change the transmission fluid.

Thus, as described, an oxidation model and a friction model are used in parallel for determining the remaining useful life of an ATF in a vehicle automatic transmission. The models are adaptable and applicable to automatic transmissions with any number of forward speeds. The process is readily executed on a transmission control module with a microprocessor and is effective in notifying the operator of the vehicle of the end of the useful life of the transmission fluid. One of the advantages of this method is that, as current determinations of remaining life for the two models are made, the current temperature data and intermediate calculation data do not need to be retained in the processor. Reference data such as penalty factors for an oxidation model and shift energy data for the friction model are retained. But with respect to ongoing calculations, only the current remaining useful life data for the two models is retained. This reduces memory requirements and increases microprocessor efficiency.

The invention has been described in terms of certain examples, but the scope of the invention is not limited to these illustrations.

What is claimed is:

1. A method of determining remaining useful life of a volume of transmission fluid in a vehicle transmission in which portions of the fluid volume are circulated from a transmission fluid sump through operating elements of said transmission including a torque converter and a torque converter clutch, the fluid having known values of remaining useful oxidation life at temperatures experienced in operation of said transmission based on a specified tolerable total increase in acid number (delta TAN), said method being performed by a programmed on-vehicle computer during continual processing cycles of said computer during transmission operation and comprising:

(a) measuring the temperature of the volume fraction of fluid, during a time increment, then located in at least one of said sump; torque converter and torque converter clutch;

(b) continually subtracting, from a current fluid remaining useful oxidation life value; incremental reductions in remaining useful fluid life due to oxidation during the time increment at the measured temperature of the volume fraction to determine a new fluid remaining useful oxidation life value for use as current fluid remaining useful oxidation life value in the next processing cycle of said computer;

(c) continually recording gear shifts executed by said transmission during a time increment and calculating shift energy input to said fluid during said increment;

(d) continually subtracting, from a current fluid remaining useful gear shift life value, incremental reductions in fluid remaining useful gear shift life due to current shift energy input to determine a reduced fluid remaining useful gear shift life value for use as current fluid remaining useful gear shift life value in the next processing cycle of said computer; and (e) producing an end-of-useful-fluid-life signal when one of the current fluid remaining useful oxidation life value or the current fluid remaining useful gear shift life value reaches zero.

2. The method of determining the remaining useful life of a transmission fluid as recited in claim 1 comprising:

($a_2$) measuring the temperature of the volume fraction of fluid, during a time increment, then located in said sump and using the temperature of the sump volume fraction to estimate a temperature for the torque converter volume fraction, and ($b_2$) continually subtracting, from a current fluid remaining useful oxidation life value, reductions in remaining useful fluid life due to oxidation during the time increment at the measured temperature of the sump volume fraction and the estimated temperature of the torque converter volume fraction to determine a new fluid remaining useful oxidation life value for use as current fluid remaining useful oxidation life value in the next processing cycle of said computer.

3. The method of determining the remaining useful life of a transmission fluid as recited in claim 1 comprising:

($a_3$) periodically measuring the temperature of the volume fraction of fluid, during a time increment, then located in said sump and using the temperature of the sump volume fraction to estimate a temperature for the torque converter volume fraction and a temperature for the torque converter clutch volume fraction, and ($b_3$) continually subtracting, from a current fluid remaining useful oxidation life value, reductions in remaining useful fluid life due to oxidation during the time increment at the measured temperature of the sump volume fraction and the estimated temperatures of torque converter volume fraction and the torque converter clutch volume fraction to determine a new fluid remaining useful oxidation life value for use as current fluid remaining useful oxidation life value in the next processing cycle of said computer.

4. The method of determining the remaining useful life of a transmission fluid as recited in claim 1 comprising:

determining an incremental reduction in fluid oxidation life for an increment of time at a reference temperature and providing a look-up table for said on-vehicle computer penalty factors for selected temperatures other than said reference temperature, and calculating incremental reductions in remaining useful fluid life due to oxidation by applying said penalty factor for the measured or estimated temperature of the fluid volume fraction.

5. The method of determining the remaining useful life of a transmission fluid as recited in claim 2 comprising:

determining an incremental reduction in fluid oxidation life for an increment of time at a reference temperature and providing a look-up table for said on-vehicle computer penalty factors for selected temperatures other than said reference temperature, and calculating incremental reductions in remaining useful fluid life due to oxidation by applying said penalty factor for the measured or estimated temperature of the fluid volume fraction.

6. The method of determining the remaining useful life of a transmission fluid as recited in claim 3 comprising:

determining an incremental reduction in fluid oxidation life for an increment of time at a reference temperature and providing a look-up table for said on-vehicle computer penalty factors for selected temperatures other than said reference temperature, and calculating incremental reductions in remaining useful fluid life due to oxidation by applying said penalty factor for the measured or estimated temperature of the fluid volume fraction.

7. The method of determining remaining useful life of a volume of transmission fluid as recited in claim 1 comprising:

(c) continually recording gear shifts executed by said transmission and transmission sump temperature during a time increment and calculating shift energy input to said fluid as a function of said sump temperature during said increment.

8. The method of determining remaining useful life of a volume of transmission fluid as recited in claim 1 comprising:

calculating a total number of gear shifts at a reference transmission sump temperature for an unused transmission fluid for a vehicle transmission;

(c) continually recording gear shifts executed by said transmission and recording average transmission sump temperature during a time increment;

continually calculating a reduction in fluid remaining useful gear shift life at said average sump temperature using a comparison of said sump temperature to said reference temperature; and (d) continually subtracting from a current fluid remaining useful gear shift life value, said reduction in fluid remaining useful gear shift life to determine a reduced fluid remaining useful gear shift life for use in the next processing cycle of said computer.

* * * * *